United States Patent
Wolf

(10) Patent No.: US 6,875,216 B2
(45) Date of Patent: Apr. 5, 2005

(54) TAPERED BIOABSORBABLE INTERFERENCE SCREW FOR ENDOSTEAL FIXATION OF LIGAMENTS

(75) Inventor: Eugene M. Wolf, San Rafael, CA (US)

(73) Assignee: Arthrex, Inc., Naples, FL (US)

( * ) Notice: Subject to any disclaimer, the term of this patent is extended or adjusted under 35 U.S.C. 154(b) by 0 days.

(21) Appl. No.: 10/634,807

(22) Filed: Aug. 6, 2003

(65) Prior Publication Data

US 2004/0097945 A1 May 20, 2004

Related U.S. Application Data

(62) Division of application No. 09/711,964, filed on Nov. 15, 2000, now Pat. No. 6,629,977.
(60) Provisional application No. 60/165,722, filed on Nov. 15, 1999.

(51) Int. Cl.[7] .............................................. A61B 17/88
(52) U.S. Cl. .................... 606/73; 606/60; 623/13.14; 623/13.18
(58) Field of Search ................... 623/12–18; 606/72–77

(56) References Cited

U.S. PATENT DOCUMENTS

| | | | |
|---|---|---|---|
| 4,950,270 A | 8/1990 | Bowman et al. | |
| 5,364,400 A | 11/1994 | Rego et al. | |
| 5,443,509 A | 8/1995 | Boucher et al. | |
| 5,456,685 A | 10/1995 | Huebner | |
| 5,470,334 A | 11/1995 | Ross et al. | |
| 5,951,560 A | 9/1999 | Simon et al. | |
| 6,113,604 A | * 9/2000 | Whittaker et al. | 606/72 |
| 6,214,007 B1 | * 4/2001 | Anderson | 606/73 |
| 6,283,973 B1 | * 9/2001 | Hubbard et al. | 606/104 |
| 6,325,804 B1 | * 12/2001 | Wenstrom et al. | 606/72 |
| 6,368,322 B1 | 4/2002 | Luks et al. | |
| 6,387,129 B2 | 5/2002 | Rieser et al. | |
| 6,436,100 B1 | 8/2002 | Berger | |
| 6,629,977 B1 | * 10/2003 | Wolf | 606/73 |

FOREIGN PATENT DOCUMENTS

EP 0556571 A 8/1993

* cited by examiner

Primary Examiner—Roy D Gibson
Assistant Examiner—Henry M Johnson, III
(74) Attorney, Agent, or Firm—Dickstein Shapiro Morin & Oshinsky LLP

(57) ABSTRACT

A bioabsorbable interference screw having a tapered profile which extends along substantially the entire length of the screw. The tapered profile makes the screw easy to insert while providing superior fixation resulting from a progressively increasing diameter. Upon insertion, the screw engages cortical bone at the back end of the bone tunnel and fills all but 5–10 mm. of the tunnel, thereby providing increased fixation strength while also promoting fast healing. The screw includes a head provided with a specially designed drive socket with radially extending slots at its outer end for receiving corresponding protrusions on the shaft of screwdriver. The drive socket optimizes the torque capacity of the screw. To maintain wall thickness, the socket has a taper corresponding to the tapered outer profile of the screw. The taper of the socket also permits easy insertion of the tip and shaft of the driver into the screw.

7 Claims, 3 Drawing Sheets

TAPERED BIOABSORBABLE INTERFERENCE SCREW FOR ENDOSTEAL FIXATION OF LIGAMENTS

This application is a division of application Ser. No. 09/711,964, filed Nov. 15, 2000, now U.S. Pat. No. 6,629,977, and claims the benefit of U.S. Provisional Application No. 60/165,722, filed Nov. 15, 1999.

BACKGROUND OF THE INVENTION

1. Field of the Invention

The present invention relates to endosteal fixation of a substitute ligament and, more specifically, to arthroscopic endosteal fixation of a substitute anterior cruciate ligament using a tapered bioabsorbable interference screw.

2. Description of the Related Art

When a ligament becomes detached from a bone, surgery usually is required to reconstruct the ligament. Often, a substitute ligament or graft is secured into bone tunnels to facilitate incorporation and permanent attachment.

Various methods of graft attachment are known, including the use of interference screws to secure the graft against the walls of a tunnel drilled through the tibia and a socket formed in the femur. A strong graft attachment is obtained by using a metal interference screw to wedge a graft bone block to the wall of a graft tunnel formed through the bone, as disclosed in U.S. Pat. No. 5,211,647 to Schmieding. If a bioabsorbable interference screw is used, the graft is often wedged directly against the bone by the screw, without a bone block.

Bioabsorbable interference screws are usually sized so that they are slightly larger that the diameter of the tunnel, so that they dilate the bone tunnel upon insertion. Dilation advantageously compacts the soft cancellous bone between the ends of the tunnel, providing better fixation. Conventional straight-sided bioabsorbable interference screws have an interference fit of about 1 mm., i.e, about 1 mm. of bone is dilated as the screw is inserted into the bone tunnel. Although it would be desirable to use larger diameter screws for increased fixation strength, larger screws have larger tips and are more difficult to align and insert correctly. Accordingly, a need exists for a bioabsorbable interference screw which provides increased dilation and interference fit without increased difficulty of insertion.

SUMMARY OF THE INVENTION

The present invention overcomes the disadvantages of the prior art and achieves the foregoing objectives by providing a tapered, elongated bioabsorbable interference screw, the taper of the screw extending along substantially the entire length of the elongated threaded screw. The taper of the bioabsorbable interference screw of the present invention advantageously facilitates insertion of the tip of the screw, while providing superior fixation resulting from a progressively increasing diameter. Upon insertion, the bioabsorbable interference screw of the present invention fills all but 5–10 mm. of the length of the tunnel, thereby providing increased fixation strength while also promoting healing.

The tapered bioabsorbable interference screw of the present invention includes a head provided with a specially designed Delta drive socket for receiving a Delta drive screwdriver or a traditional hex-head screwdriver. The unique drive socket of the interference screw of the present invention optimizes the torque capacity of the screw. To maintain wall thickness, the drive socket is tapered in correspondence with the tapered outer profile of the device. The taper also permits easy insertion of the tip and shaft of the Delta driver or hex driver (also tapered) into the fixation screw.

The tapered bioabsorbable interference screw of the present invention is preferably threaded along substantially the entire length of the screw to maximize fixation strength within the tunnel. Preferably, the distal end of the screw, the end closest to the joint, has a smooth, rounded tip profile so as to minimize abrasion with the graft.

The interference screw of the present invention may be optionally provided with a cannulation for insertion over a guide pin. In this embodiment of the invention, a cannulated Delta drive or hex drive screwdriver is used to insert the screw into the tunnel over the guide pin The bioabsorbable interference screw of the present invention is preferably formed of highly crystalline poly-(L-lactic acid) (PLLA) compound.

In the preferred method of ACL reconstruction of the present invention, the graft, preferably a hamstring tendon autograft or allograft, is secured, preferably by interference screw fixation, in a femoral socket formed through the tibial tunnel, as described, for example, in U.S. Pat. No. 5,320,626, the disclosure of which is incorporated herein. The hamstring graft is then drawn taut and secured in the tibial tunnel by insertion of the tapered bioabsorbable interference screw of the present invention. If the interference screw is fully cannulated, a guide pin may optionally be employed to guide the interference screw during delivery and installation.

Other features and advantages of the present invention will become apparent from the following description of the invention which refers to the accompanying drawings.

DETAILED DESCRIPTION OF THE PREFERRED EMBODIMENT

Figure 1:
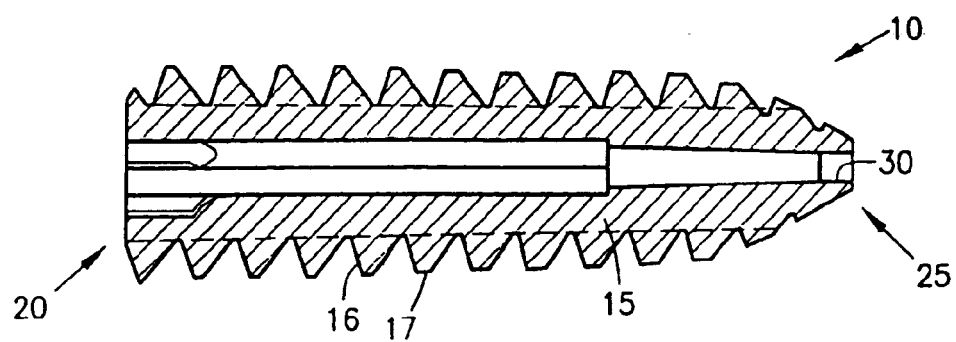
FIG. 1 is a cross-sectional detail view, drawn along line A—A of FIG. 2, of the tapered bioabsorbable interference screw of the present invention.

Referring to FIG. 1, a cross-sectional view of the tapered bioabsorbable interference screw 10 of the present invention is shown. Screw 10 is preferably formed of a bioabsorbable material, such as PLA or PLDLA (Poly(L/D-lactide)Acid). Screw 10 has a main body portion 15, a proximal end 20, and a distal end 25, and is preferably provided with a cannula 30.

Screw 10 is provided in a preferred length of 35 mm., with threads 16 extending substantially from proximal end 20 to distal end 25. The edges 17 of the thread(s) 16 are flattened to prevent severing tissue during screw insertion.

Figure 2:
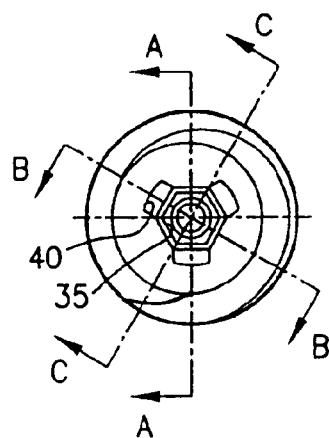
FIG. 2 is a rear elevational view of the tapered bioabsorbable interference screw of the present invention.

Referring to FIG. 2, the proximal end 20 of screw 10 is provided with an elongated socket 35 configured to receive a Delta drive screwdriver 56, described below. To that end, socket 35 is provided, at its outer end, with radially-extending slots 40 in every other annular face of socket 35. The slots 40 receive correspondingly-shaped protrusions 42 (shown in FIGS. 5A and 5B) on the proximal end of the shaft 58 of driver 56. The Delta drive socket 35 permits increased torque capacity while minimizing the problem of stripping the drive portion of the screw 10. Advantageously, the Delta drive socket can also be used with a traditional hex drive screwdriver.

Figure 3:
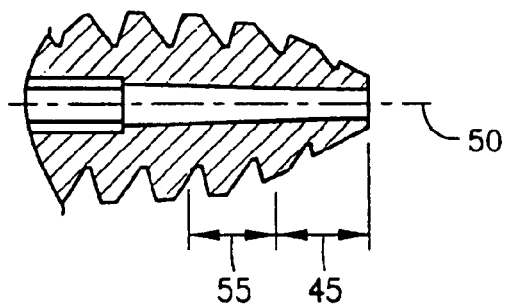
FIG. 3 is a cross-sectional detail view, drawn along line C—C of FIG. 2, of the interference screw of the present invention.
Figure 4:
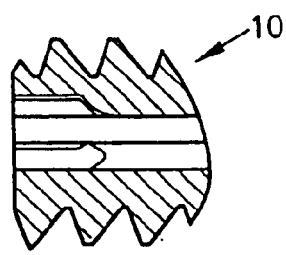
FIG. 4 a cross-sectional detail view, drawn along line D—D of FIG. 2, of the interference screw of the present invention.

Referring to FIGS. 1 and 3, screw 10 is tapered. The taper is a complex taper with an initial portion 45 at an angle of about 27° with respect to the longitudinal axis 50, an intermediate portion 55 at an angle of about 12° angle with respect to axis 50, and an elongated main body 15 with a more gradual taper. The relatively pointed distal portion 45 forms a nose that provides for easy insertion of the screw 10 into a bone tunnel.

The interference screw of the present invention is preferably provided in four sizes: (1) a screw which tapers from a 7.5 mm. diameter at its tip to 9 mm. at the socket; (2) a screw which tapers from a 8.5 mm. diameter at its tip to 10 mm. at the socket; (3) a screw which tapers from a 9.5 mm. diameter at its tip to 11 mm. at the socket; and (4) a screw which tapers from a 9.5 mm. diameter at its tip to 12 mm. at the socket.

As screw 10 threadingly advances through a bone tunnel, the screw dilates bone outwardly around the bone tunnel and creates an interference fit therewith. The tapered body of the screw permits the use of a smaller tunnel, as compared with non-tapered bone screws. The taper also causes a wedge effect that allows a large-diameter screw to be used in relation to the bone tunnel and graft size. The present interference screw promotes about a 1.5 mm interference fit; i.e., the diameter of the proximal end 20 of the screw 15 is 1.5 mm larger than the diameter of the bone tunnel. Typical bone screws, which are not tapered, provide a maximum of 1.0 mm interference fit. The additional interference provides 28% more pull out strength.

Screw 10 is configured to be sufficiently long so as to fill all but the top 5–10 mm of the tibial bone tunnel. This configuration secures a large portion of the ligament graft against the bone tunnel while also providing threading engagement of the threads 16 of screw 10 against cortical bone at outer end of the bone tunnel. Because cortical bone is significantly harder than the interior soft, cancellous core, cortical bone provides significantly more load bearing capability. As a result, the invention eliminates the need for multiple, shorter interference screws in a bone tunnel.

Figure 5A:
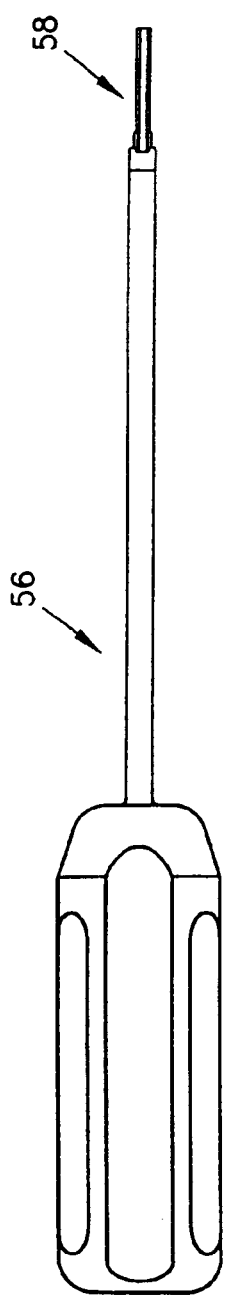
FIG. 5A is a side view of the interference screw driver and FIG. 5B is a detailed view of the tip of the driver.
Figure 5B:
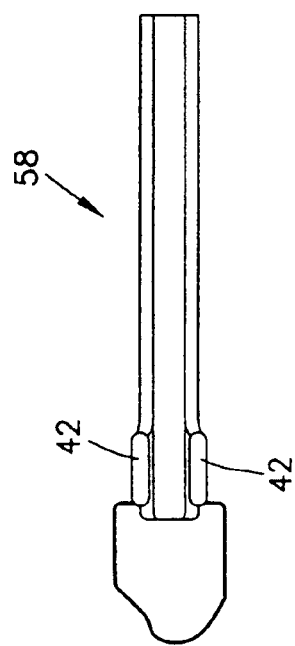

FIGS. 5A and 5B show the driver 56 for inserting interference screw 10. Driver 56 has an taped elongated hexagonally shaped shaft 58 at its distal end, best shown in the magnified view of FIG. 5B, which is provided with protrusions 42 to mate with the Delta drive recess 35 of screw 10.

Figure 6:
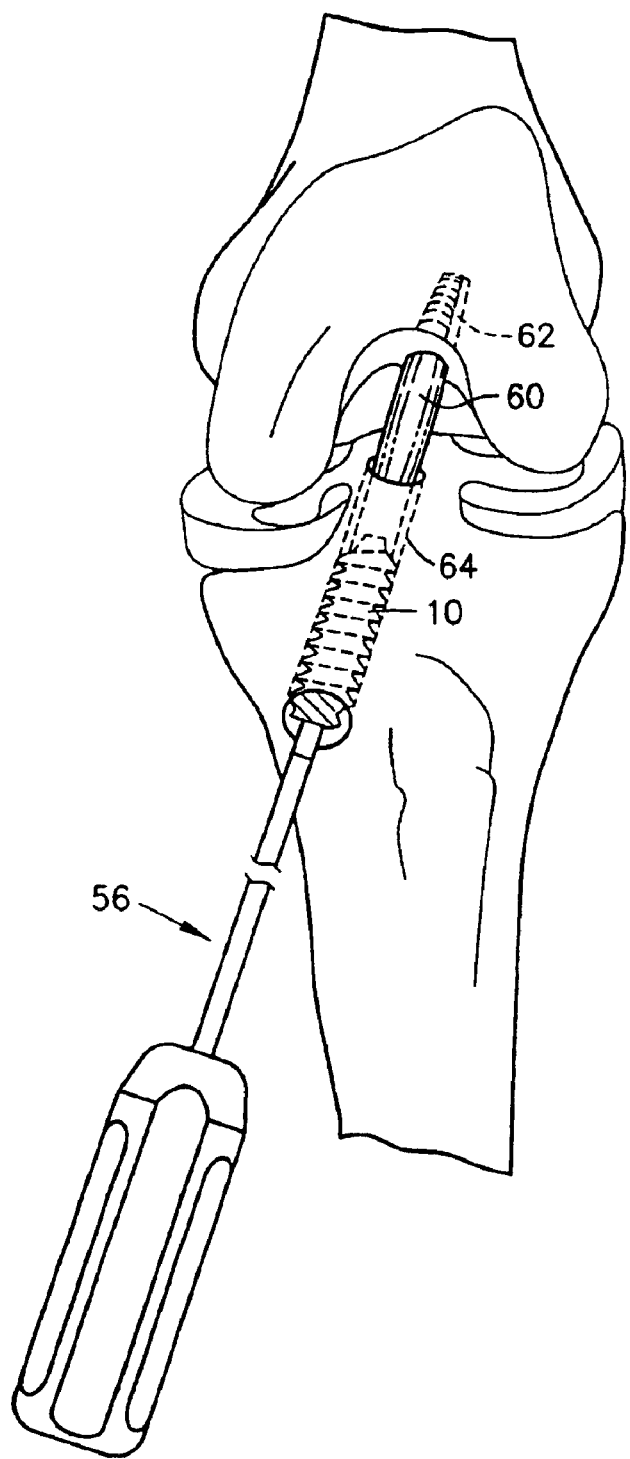
FIG. 6 shows the interference screw of the present invention being inserted into the tibial tunnel against a ligament graft.

Referring to FIG. 6, the method of endosteal fixation of a ligament graft using the bioabsorbable interference screw of the present invention includes the steps of securing one end of a graft 60 in the femoral socket 62, pulling the opposite end of the graft (extending through the tibial tunnel) taut, and fixating the graft 60 in the tibial tunnel 64 by mounting the bioabsorbable interference screw 10 on driver 56 and, using the driver, driving screw 10 in the tibial tunnel against graft 60 to the level of the anterior cortex in the distal portion of the tibial tunnel, such that the interference screw fills all but the top 5–10 mm. of the tunnel. Driver 66 is then removed, leaving screw 10 in place with an interference fit of up to 1.5 mm.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A bioabsorbable interference screw for ACL reconstruction, comprising:

an elongated threaded body having a proximal end, a distal end, a length of about 35 mm. and a taper, the threads and the taper of the elongated threaded body extending along substantially the entire length of the elongated threaded body, the proximal end of the screw being configured to provide an interference fit of up to 1.5 mm. in a bone tunnel;

a tip disposed of the distal end of the elongated body, the tip being threaded and having a taper which is greater than the taper of the elongated threaded body so as to be easily insertable in a bone tunnel; and a drive socket disposed within the screw and extending from the proximal end of the elongated threaded body, wherein the drive socket has radially-extending slots for receiving a driver having three radially-extending protusions corresponding to the slots.

2. The bioabsorbable interference screw of claim 1, wherein the drive socket has a taper corresponding to the taper of the elongated threaded body.

3. The bioabsorbable screw of claim 1, wherien the screw is fully cannulated for receiving a guide pin.

4. The bioabsorbable interference screw of claim 1, wherein the screw tapers from a diameter of 9 mm. at the drive socket to a diameter of 7.5 mm. at the tip.

5. The bioabsorbable interference screw of claim 1, wherein the screw tapers from a diameter of 10 mm. at the drive socket to a diameter of 8.5 mm. at the tip.

6. The bioabsorbable interference screw of claim 1, wherein the screw tapers from a diameter of 11 mm. at the drive socket to a diameter of 9.5 mm. at the tip.

7. The bioabsorbable interference screw of claim 1, wherein the screw tapers from a diameter of 12 mm. at the drive socket to a diameter of 9.5 mm. at the tip.

* * * * *